US00PP09879P

United States Patent [19]

Jacobsen

[11] Patent Number: Plant 9,879

[45] Date of Patent: Apr. 29, 1997

[54] POINSETTIA PLANT PETERSTAR PINK

[75] Inventor: Peter Jacobsen, deceased, late of Skibby, Denmark, by Aase Jacobsen, executrix

[73] Assignee: Paul Ecke Ranch, Inc., Encinitas, Calif.

[21] Appl. No.: 500,486

[22] Filed: Jul. 10, 1995

[51] Int. Cl.[6] ..... A01H 5/00

[52] U.S. Cl. ..... Plt./86.3

[58] Field of Search ..... Plt./86.3

[56] References Cited

U.S. PATENT DOCUMENTS

P.P. 8,274 6/1993 Jacobsen ..... Plt./86.3

P.P. 9,336 10/1995 Beckman ..... Plt./86.3

P.P. 9,385 11/1995 Zerr ..... Plt./86.3

*Primary Examiner*—James R. Feyrer

*Attorney, Agent, or Firm*—Arnold, White & Durkee

[57] ABSTRACT

Poinsettia 'Peterstar Pink' is a new cultivar, distinguished by dark pink bracts, large flowers, strong stems and self-branching characteristics. 'Peterstar Pink' is a sport of the red bracted 'Peterstar' (U.S. Pat. No. P.P. 8,259) with the same flowering response and cultural requirements. The new plant produces a very desirable branched flowering pot plant. The new plant is resistant to epinasty after being confined to shipping containers. The post-production foliage and bract retention is good.

1 Drawing Sheet

BACKGROUND OF THE NEW PLANT

The new poinsettia cultivar originated as a pink bracted sport of 'Peterstar' (U.S. Pat. No. P.P. 8,259) in my greenhouse in Skibby, Denmark in 1991. It was induced through irradiation of vegetative plants with 2500 rads of gamma radiation, and was selected from about 200 mutants so produced, because of its dark pink bracts, large flowers, strong stems, self-branching, and dark green leaves, traits which help distinguish it from other poinsettia cultivars, and seemed to make it a desirable plant for commercial greenhouse production. 'Peterstar Pink' differed from its parent 'Peterstar' in having dark pink bracts as compared to the bright red bracts of 'Peterstar'. 'Peterstar Pink' resembles poinsettia '15-84' (U.S. Pat. No. P.P. 7,310) but distinctly differs in the following traits. 'Peterstar Pink' has a more compact growth habit and flowers earlier phenotypically, 'Peterstar Pink' resembles its parent 'Peterstar' (U.S. Pat. No. P.P. 8,259) except for those traits associated with color mutations. The morphology, plant vigor and flowering response times are very similar. The flower bract color of 'Peterstar Pink' is dark pink, R.H.S. 51A for the small inner bracts and R.H.S. 51B for the larger outer bracts. The red bract color of 'Peterstar' is near R.H.S. 46B. The leaf petiole color of 'Peterstar' is light green, that of 'Peterstar' is red.

The foliage and bract colors of 'Peterstar Pink' are distinctly darker than known poinsettias of similar derivation. Leaf color, darker than R.H.S. 147A, and bract color, R.H.S. 51B for large bracts and R.H.S. 51A for smaller bracts are darker than those for 'Pegirl' (U.S. Pat. No. P.P. 8,274). The flower bract color "dark pink", differs from both 'Beckmann's Altrosa' (U.S. Pat. No. P.P. 9,336) and 'Fisflirt' (U.S. Pat. No. P.P. 9,385) described as pink with a slight salmon cast and salmon pink, respectively. With respect to flowering response time, 'Peterstar Pink' flowers at almost the same time under natural daylight conditions as 'Beckmann's Altrosa' and 4–5 days earlier than either 'Pegirl' or 'Fisflirt'. Plant height of flowering plants is comparable for 'Peterstar Pink' and 'Beckmann's Altrosa'. Both are shorter than 'Pegirl'.

After selection, 'Peterstar Pink' was vegetatively reproduced from stem cuttings for test purposes in Encinitas, Calif. By subjecting clones of this plant to successive generations of vegetative propagation, it was demonstrated that the distinctive characteristics of 'Peterstar Pink' held true from generation to generation. Grown under the same greenhouse environment, 'Peterstar Pink' had the same growth habit and flowering response time as the parent plant 'Peterstar'.

DESCRIPTION OF THE PHOTOGRAPHS

Poinsettia 'Peterstar Pink' is illustrated in the accompanying color photographs.

The upper photo is a side view of 3 single stem plants per pot in full flower.

The lower photo is a top view of the same plants showing flower and bract formation.

DESCRIPTION OF THE PLANT

The following is a detailed description of this new poinsettia as observed in Encinitas, Calif., U.S.A. during December 1994. Observations were recorded from flowering plants, grown as 3 single stem plants per pot. The pot was 14 cm in diameter and 11 cm in height. Color designations are compared to the 1986 edition of R.H.S. Colour Chart, first published in 1966 by The Royal Horticultural Society, London, England.

THE PLANT

The following chart summarizes some of the differences between 'Peterstar Pink' and poinsettia '15-84'.

| Plant | 'Peterstar Pink' | '15–84' |
|---|---|---|
| Internode Length | 16–17 mm | 20 mm |
| Height | 35 cm | 44 cm |
| Flower Response | 8.5 weeks | 9 weeks |
| Blooming date (Southern California) | November 25 | November 30 |
| Flowers | Sterile | Fertile |

Chart 2 illustrates several differences between 'Peterstar Pink' and known poinsettias of similar derivation.

CHART 2

| 'Peterstar Pink' | 'Pegirl' | 'Beckmanns Altrosa' | 'Fisflirt' |
|---|---|---|---|
| Leaf: | | | |
| upper: darker 147A | 47A-B | 137A | 147A-137A |
| under: 147B | 147B-C | 137C | 147B |
| Bract: | | | |
| upper: 51A and 51B | 50B-C | 50B | 52C-D |
| under: 51B-C | 51C-D | 47D | |
| Leaf Petiole: | | | |
| light green | green | light red | light green |

Origin: Sport of 'Peterstar' (U.S. Pat. No. P.P. 8,259), induced through irradiation of vegetative plants with 2500 rads of gamma radiation.

Classification:

*Botanic.*—*Euphorbia pulcherrima* Willd.

*Common name.*—Poinsettia.

*Cultivar name.*—'Peterstar Pink'.

Form: Shrub.

Height: Medium.

Growth habit: As a single stemmed plant, upright and vigorous with self-branching side shoots. The application of a chemical growth retardant may not be needed to restrict height for commercial pot plant production. I observed 3 unpinched plants in a pot with an overall height of 35 cm and an overall width of 45 cm. The bract diameter of individual flowers was 30 cm. compactness of 'Peterstar Pink' is demonstrated by the internode length. The internode lengths of flowering plants of 'Peterstar Pink' are 16–17 mm.

Branching: Axillary branches will develop and terminate in a flower without pinching. However, it is usually desirable to pinch 'Peterstar Pink' before flower induction and remove all terminal dominance. Then, all axillary branches will develop uniformly and at a faster rate.

Growth rate: Rooting of stem cutting occurs in 12–18 days under intermittent mist.

Flowering: The plant will flower in eight to nine weeks under continuous long night conditions and night temperatures of about 16°–18° C. Like its parent, ('Peterstar'), 'Peterstar Pink' will be in full bloom in late November in the Southern California under natural day-length conditions.

Foliage: The foliage is clean and uniformly dark green from bottom to top of the plant. The leaves are of medium size, leaf blades typically being 13–14 cm long and 8–9 cm wide with leaf petioles 4–6 cm long.

*Leaf shape.*—Typical leaves are ovate with obtuse bases and acuminate tips. Leaf margins are mostly entire. An occasional lower leaf is modestly lobed on either side of the leaf blade.

*Leaf surface.*—The upper surface is glabrous and the under surface is slight pubescent.

*Color.*—Upper side — Green, slightly darker than R.H.S. 147A. Under side — Green, near R.H.S. 147B.

*Retention.*—The foliage retention is good even under low light intensities in the consumer's home.

Bracts: Generally there are 17–21 pink bracts of various sizes subtending the cyathia. The primary bracts have blades typically 14–16 cm long and 10–11 cm wide with petioles 2–3 cm long.

*Shape.*—Primary bracts are ovate with acute bases and acuminate tips. Leaf margins are entire or weakly lobed with 1 small indention on either side of the bract. Secondary bracts are ovate to elliptic and have entire margins.

*Surface.*—The bract surface is slightly rugose.

*Color.*—Upper side — Dark pink with slightly darker veins and lighter bract margins. The smaller center bracts are darker than the primary bracts, with the same vein color. Primary bracts near R.H.S. 51B; small bracts and veins near R.H.S. 51A. Under side — Pink, near R.H.S. 5B-C.

Flowers: Generally, 18–22 cyathia (flowers) are present when the plant is in full bloom. Each cyathium is about 6–7 mm long and 5–6 mm wide, green in color, and fringed crimson at the distal end. Usually one, but occasionally two yellow nectar cups protrude from the side of each cyathium. The flower pedicel is also green and about 5 mm in length. The stamens protruding from the cyathia are crimson and trifurcate. 'Peterstar Pink' has abortive anthers, is male sterile and possible female sterile, as seed set has not been seen on this cultivar. Cyathia retention was about three weeks beyond the time the flower was fully mature.

*Nectar exudate.*—Present, abundant.

*Seed formation.*—Self-incompatible.

*Fertility.*—Flowers may be sterile.

Post production: 'Peterstar Pink' was resistant to epinasty after being confined to shipping containers. The foliage and bract retention was good.

What is claimed is:

1. A new and distinct poinsettia cultivar, substantially as herein shown and described, distinguished by its strong stems, dark pink bracts, self-branching, large flowers and good leaf and bract retention in the consumer environment.

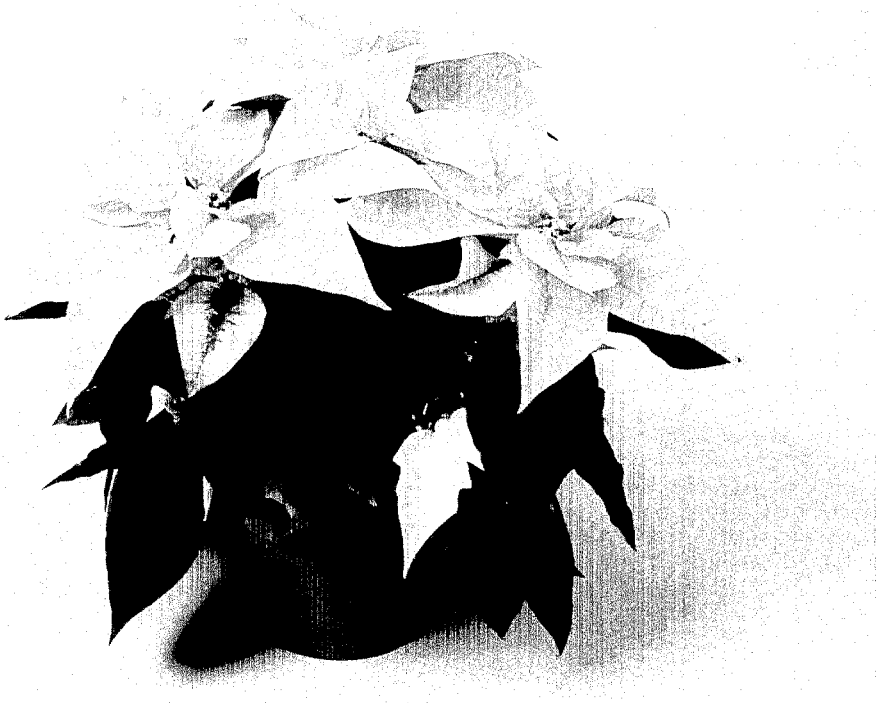
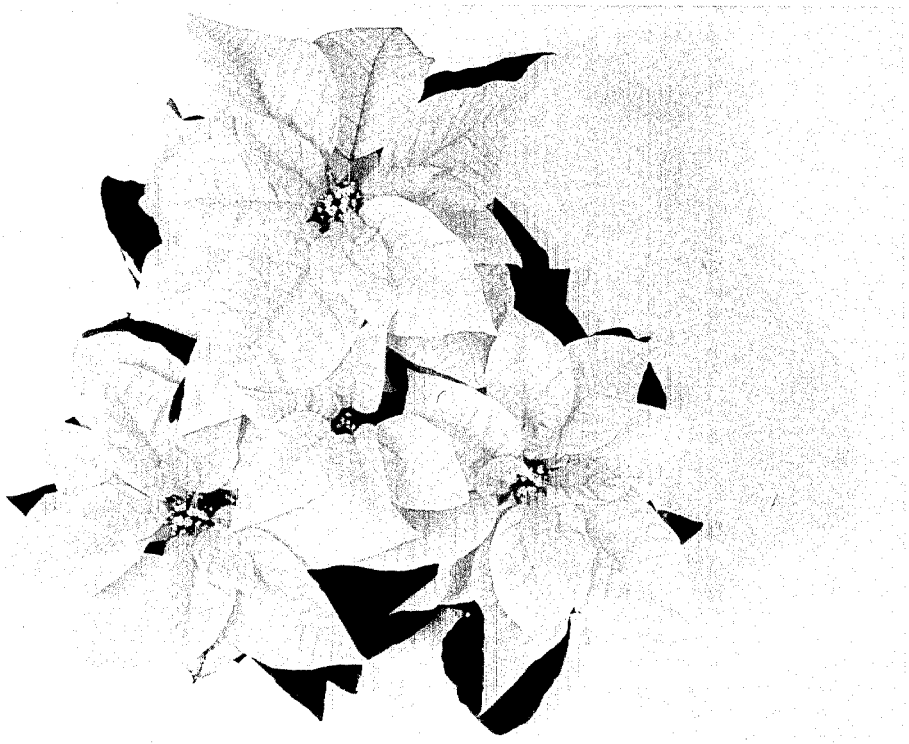

* * * * *